United States Patent [19]

Matsumoto et al.

[11] Patent Number: 5,032,509
[45] Date of Patent: Jul. 16, 1991

[54] METHOD OF PREPARING GALCATOOLIGOSACCHARIDE

[75] Inventors: Keisuke Matsumoto; Yoichi Kobayashi; Tatsuhiko Kan, all of Tokyo, Japan

[73] Assignee: Kabushiki Kaisha Yakult Honsha, Tokyo, Japan

[21] Appl. No.: 416,459

[22] Filed: Oct. 3, 1989

[30] Foreign Application Priority Data

Oct. 6, 1988 [JP] Japan .................. 63-251040
Oct. 21, 1988 [JP] Japan .................. 63-264009

[51] Int. Cl.$^5$ .................. D23C 9/12; C12P 39/00; C12P 19/04; C12P 19/24
[52] U.S. Cl. ................................ 435/42; 127/30; 127/31; 426/42; 426/43; 435/72; 435/94; 435/97; 435/101
[58] Field of Search .............. 435/42, 94, 97, 101, 435/72; 426/42, 43; 127/30, 31

[56] References Cited

U.S. PATENT DOCUMENTS 4,944,952  7/1990  Kobayashi et al. .................. 426/42

FOREIGN PATENT DOCUMENTS 070535  6/1975  Japan .
236790  10/1986  Japan .
130695  6/1987  Japan .

OTHER PUBLICATIONS

Biotech Abs. 89-09061 Abril et al., J. Sci. Food Agric., (1989), 48, 4, 511-514.
Biotech Abs. 86-09609, Chiu et al., J. Dairy Sci., (1986), 69, 4, 959-964.

Primary Examiner—Herbert J. Lilling
Attorney, Agent, or Firm—Oblon, Spivak, McClelland, Maier & Neustadt

[57] ABSTRACT

A method of preparing a mixture of galactooligosaccharides having the following formula:

Gal-(Gal)n-Glc where Gal represents a galactose residue, Glc represents a glucose residue, and n represents an integer between 1 and 4, and monosaccharides by having microorganisms containing β-galactosidase or β-galactosidase act on lactose, the method comprising:
having glucose isomerase coexist in a liquid to be reacted or adding glucose isomerase after completion of the reaction, whereby a portion of glucose prepared by the β-galactosidase processing is converted into fructose. Then, sweetener is prepared by separating monosaccharides from the mixture.

11 Claims, No Drawings

METHOD OF PREPARING GALCATOOLIGOSACCHARIDE

BACKGROUND OF THE INVENTION

The present invention relates to a method of preparing galactooligosaccharides having a function of promoting the growth of bifidobacterium, that is, galactooligosaccharides expressed by a general formula Gal-(Gal)n-Glc (where Gal represents a galactose residue, Glc represents a glucose residue, and n represents an integer between 1 and 4), the method being able to prepare superior yields of galactooligosaccharides from lactose. More particularly, the present invention relates to a method of preparing a sweetener from lactose.

In the dairy industry, a great quantity of whey is obtained as a by-product when butter, cheese, casein protein, or whey protein is prepared from cow's milk or goat's milk. Worldwide the quantity of cheese whey alone is estimated to reach a hundred million metric tons. However, only a small proportion of less than 5% of that whey has been utilized effectively, the residual whey being disposed of. This leads to critical environmental problems in the dairy industry. Therefore, the effective use of whey, and more particularly, of lactose which is about 80% of the overall solids in whey has been desired by dairy nations in terms of the practical use of unused resources and solution of the environmental problems.

Whey and lactose therefrom have been conventionally utilized so as to be added to dietary products or drugs, and are further utilized for manufacturing syrup sweeteners and galactooligosaccharides functioning to promoting the growth of bifidobacterium.

Galactooligosaccharides have been manufactured from lactose in such a manner that $\beta$-galactosidase of Aspergillus is allowed to act on lactose as disclosed in Japanese Patent Publication No. 58-20266, and in another manner such that Cryptococcus yeast is utilized as in Japanese Patent Laid-Open No. 61-236790. However, these methods which utilize the $\beta$-galactosyl transfer reaction performed by $\beta$-galactosidase suffer from a poor yield of galactooligosaccharide, the yield of the galactooligosaccharide from lactose stopping at a poor proportion of about 30%. Problems of this type are considered to be caused by the interruption action of monosaccharides which are produced secondarily. That is, monosaccharides can be secondarily produced by the hydrolytic reaction which takes place simultaneously with the $\beta$-galactosyl transfer. Glucose which is the principle ingredient of the thus produced monosaccharides serves as an acceptor of the $\beta$-galactosyl transfer, causing transfer disaccharides to be produced. Therefore, this transfer action competes with the transfer reaction which produces oligosaccharides. Furthermore, the monosaccharides inhibit the activity of the $\beta$-galactosidase, causing the speed of the transfer reaction to be lowered. The quantity of the production of galactooligosaccharides reaches its maximum rate when the concentration of lactose serving as the substrate of the reaction is halved or lowered with respect to the concentration at the time of supplying the lactose. However, the concentration of monosaccharide in the solution rises in accordance with the progress of the reaction, causing the interruption to become considerable. As a result, the reaction time is lengthened and other secondary reactions take place.

Furthermore, since the product obtained from the reaction contains a large quantity of non-reacted lactose, monosaccharides which have been secondarily produced due to the hydrolytic reaction, as well as transfer disaccharides generated from the thus-produced monosaccharides, the content of the desired galactooligosaccharides is not satisfactory.

Therefore, methods to improve the yield of galactooligosaccharides with respect to lactose and to raise the content of oligosaccharides in the product obtained from the reaction have been studied. As a result, a method was disclosed in Japanese Patent Laid-Open No. 62-130695, the method being characterized in that a product in which galactooligosaccharides are contained at a considerably high degree can be obtained by allowing the reaction in which the galactooligosaccharides are produced to progress while the glucose and galactose produced by a reaction when allowing Cryptococcus yeast to act on lactose are consumed by other yeasts. However, in this method in which the reaction is allowed to progress with the monosaccharides secondarily produced during the reaction being consumed by yeast, large quantities of glucose and galactose are consumed by microorganisms without being effectively used, and the intended improvement in the yield of galactooligosaccharides from lactose cannot be achieved. Also a large quantity of yeast is required and work for removing the yeast must also be conducted after completion of the reaction. In addition, as refining work for removing the metabolite of yeast from the reacted product and other work for removing waste yeast are necessary cost is also raised.

Furthermore, the above-described interruption of the transfer reaction by monosaccharides becomes excessive as in the concentration of monosaccharides rises. Therefore, the attempt made to improve the efficiency of the reaction by raising the concentration of lactose which is the raw material in the liquid to be reacted is interrupted.

For the preparation of sweetener from lactose, there is a process wherein lactose which is worthless as a sweetener since it has a poor relative degree of sweetness with respect to that of saccharose is hydrolyzed so that glucose and galactose each of which has a high degree of sweetness are prepared. The hydrolyzing of lactose is conducted by an acid hydrolysis method and an enzyme method. As the former method requires severe conditions in the reaction thereof, not only are expensive facilities necessary but further the separation and refining of the product resulting from the hydrolysis cannot be achieved easily. Therefore, an enzyme method using $\beta$-galactosidase has been widely used recently. Although the enzyme method only needs moderate reacting conditions, a large quantity of enzymes must be used in order to completely conduct the hydrolysis. Furthermore, the reaction in the enzyme method must be conducted under conditions of low lactose concentrations of 4 to 10% in order to prevent the progress of the saccharide transfer reaction which is the secondary reaction. Therefore, a large reacting apparatus and syrup condensing apparatus are necessary, increasing the cost needed for the condensation, etc. Furthermore, the degree of sweetness which can be theoreticallyachieved is at most about 0.6 even if glucose and galactose of the same mole are prepared by completely hydrolyzing lactose. Furthermore, the quality of sweetness of the sweet syrup obtained is far inferior to sugar and is not very appealing.

In order to overcome this, a method with which the degree of sweetness of the syrup can be raised and the quality of sweetness can be improved was disclosed in Japanese Patent Laid-Open No. 50-70535, the method being characterized in that glucose isomerase is allowed to act on syrup obtained by hydrolyzing lactose so as to convert glucose into fructose displaying significant sweetness. However, since the conversion ratio from glucose into fructose is at most 50% and galactose of low sweetness remains as it is, the degree of sweetness of the overall syrup is at most about 0.7 to 0.8 and the quality of the sweetness is not satisfactory.

Syrup containing the same amount of galactose as glucose also raises physiological problems as a sweetener. That is, although galactose is a necessary component of the human body, the intake of large qauntities of galactose can prove fatal for a person suffering from galactosemia, those who lack a metabolic function for converting an intake of galactose into glucose. Furthermore, galactose is considered to be a cause of cataracts in infants and the elderly whose galactose metabolism is insufficient, and should thereby avoid the intake thereof.

To this end, an object of the present invention is to overcome the above-described problems arising when galactooligosaccharides are prepared from lactose by utilizing the action of β-galactosidase (or microorganisms containing enzymes of this type).

Another object of the present invention is to provide a method of preparing syrup sweetener capable of overcoming the above-described problems which arise when sweetener is prepared from lactose, the obtained syrup sweetener displaying a low degree of galactose content and exhibiting both an excellent degree of sweetness and excellent quality of sweetness.

SUMMARY OF THE INVENTION

That is, an aspect of the present invention lies in a method of preparing a mixture of galactooligosaccharides having the following formula:

Gal-(Gal)n-Glc where Gal represents a galactose residual, Glc represents a glucose residue, and n represents an integer ranged between 1 and 4, and monosaccharides by having microorganisms containing β-galactosidase or β-galactosidase act on lactose, wherein a portion of glucose prepared by the β-galactosidase treatment is converted into fructose by making glucose isomerase exist in liquid to be reacted or adding glucose isomerase after completion of the reaction.

Another aspect of the present invention lies in a method of preparing a sweetener comprising: preparing a mixture of galactooligosaccharides having a following formula:

Gal-(Gal)n-Glc where Gal represents a galactose residue, Glc represents a glucose residue, and n represents an integer ranged between 1 and 4, and monosaccharides by allowing microorganisms containing β-galactosidase or β-galactosidase to act on lactose, wherein a portion of glucose prepared by the β-galactosidase treatment is converted into fructose by making glucose isomerase exist in liquid to be reacted or adding glucose isomerase after completion of the reaction, and then separating monosaccharides whose main principle ingredients are glucose and fructose from the mixture.

DETAILED DESCRIPTION OF THE INVENTION

According to the present invention, β-galactosidase having a galactosyl transfer reaction activity is utilized to serve as enzyme to hydrolyze lactose. As a result, glucose and galactose are prepared from lactose, and galactooligosaccharides expressed by a general formula Gal-(Gal)n-Glc (where Gal represents a galactose residue, Glc represents a glucose residue, and n represents an integer ranged between 1 and 4) are also prepared. The β-galactosidase needs to be of a type having strong transfer activity so as to convert, at a high rate, galactose residue of lactose into galactooligosaccharides, the high rate conversion preventing generation of free galactose. Simultaneously with or after completion of the reaction using β-galactosidase, glucose isomerase is allowed to act on glucose prepared by the above-described reaction using the β-galactosidase so as to convert a portion of the glucose into fructose.

According to the present invention, since a large portion of the galactose residue of raw material lactose can be converted into galactooligosaccharides, the obtained product displays a high rate of galactooligosaccharide content and monosaccharides which are secondarily prepared contain reduced quantities of galactose, the monosaccharides being therefore mostly composed of glucose and fructose.

The method of preparing galactooligosaccharides according to the present invention is preferably arranged such that glucose isomerase coexists in the liquid to be reacted when galactooligosaccharides are prepared by having microorganisms containing β-galactosidase or β-galactosidase act on lactose.

The thus coexisting glucose isomerase in the liquid to be reacted according to the method of the present invention successively isomerizes glucose prepared due to the hydrolyzing of lactose so as to convert it into fructose. As a result, the transfer reaction is protected from an interruption by accumulated glucose in the liquid to be reacted. Therefore, it is effective for glucose isomerase to coexisted with β-galactosidase so as to be allowed to act simultaneously with it. Successive action of glucose isomerase cannot improve on the yield of galactooligosaccharides.

Glucose isomerase of any derivative can be used. For example, GODO-AGI (manufactured by Godo Shusei Co., Ltd.), Sweet Zym (manufactured by Novo Industri A.S.), or TOYO-GI (manufactured by Toyo Jozo Co., Ltd.) can be used.

It is preferable that the quantity of glucose isomerase is determined to be a value which is necessary to immediately convert glucose prepared due to the action of β-galactosidase into fructose. However, excessive use thereof does not cause any problems.

β-galactosidase of any derivative can be used. For example, those derived from mold such as *Aspergillus oryzae* and *Aspergillus niger;* those originated from yeast such as *Bullera Singularis,* Candida, and Klyveromyces; those originated from bacteria such as *Bacillus circulans, Lactobacillus bulgaricus,* and *Streptococcus thermophilus* can be used. Furthermore, enzymes of *Cryptococcus lowrenty* as disclosed in Japanese Patent Laid-Open No. 62-111685 can be used. Commercial β-galactosidase such as Maxilact (manufactured by Gistprocade Co., Ltd.), Lactaze Y400 (Yakult Honsha Co., Ltd.), Lactozym (Novo Industri A.S.), GODO-YNL (Godo Shusei Co., Ltd.), and Biolacta (Daiwa Chemicals Co., Ltd.) can be used.

Although the quantity of β-galactosidase used in the method according to the present invention is not limited in particular, normally about 1 to 100 units per 1g lactose and preferably about 3 to 50 units are used.

The two enzymes can be used as a solution or in the form of an immobilized enzyme. In addition, microorganisms containing each enzyme can be used in the reaction, the microorganisms capable of being used in immobilized microorganisms.

Lactose treated with β-galactosidase may be in any form such as whey, its condensed liquid, lactose for food, or mixtures thereof. It is preferable in order to achieve the objects of the present invention that the concentration of lactose be considerably high, since the higher the concentration becomes, the more the galactosyl transfer reaction takes precedence over the hydrolysis reaction. Although the solubility of pure lactose at room temperature is not considerably high, it can be significantly dissolved in hot water and its supersaturated state can be easily generated. Therefore, lactose can be dissolved up to about 70% (in weight percent: hereinafter) if suitable conditions are provided. The higher the concentration of lactose, the higher the upper temperature limit at which enzymes can react becomes, enabling high temperature treatment of high reaction speed. Therefore, the lactose solution should be heated up to a high temperature within the range in which the enzymes can act on the lactose solution, preferably carrying out the processing with enzymes such that the lactose solution is heated to 30° to 70° C. with a lactose concentration of 10% or more, preferably 20 to 65%.

Glucose prepared by processing with β-galactosidase is converted into fructose showing a high degree of sweetness by using glucose isomerase.

It is preferable that the glucose isomerase is immediately allowed to act on glucose formed from lactose hydrolysis with the glucose isomerase allowed to exist in the mixture to be processed, glucose isomerase being allowed to exist during the treatment by using β-galactosidase. By virtue of the simultaneous reaction method, the reaction speed can be made faster than the reaction speed realized by the successive reaction method in which the isomerization by means of glucose isomerase is arranged to be an individual processing. Furthermore, the rate of transfer of galactose can be raised, causing the quantity of production of free galactose to be reduced. As a result, an excellent yield of glucose and fructose can be prepared. The reason the above-described advantages can be obtained from the simultaneous reaction is considered to lie in that the accumulation of glucose in the reaction system is restricted due to the successive conversion of glucose which is one of the products prepared from the transfer reaction into fructose. As a result, the equilibrium of the transfer reaction is shifted to the product side, causing lactose to be reduced and the quantity of galactooligosaccharide and monosaccharide production to be increased. Furthermore, since the concentration of glucose is maintained at a low level, the probability of the preparation of transfer disaccharides due to the transfer of galactose into glucose is lowered. The transfer of galactose into fructose prepared from glucose can be prevented with respect to glucose.

In the case of this simultaneous reaction, the reaction condition must be arranged such that two types of enzymes can act simultaneously. Alternatively, β-galactosidase and glucose isomerase whose preferable usage conditions are not change considerably need to be combined. When the reaction starts under preferable conditions, glucose, fructose, and galactooligosaccharides increase linearly in the reaction system in accordance with the progress of the reaction. Then, the reaction displays a considerably complicated change such that galactooligosaccharides are gradually reduced from a certain time. Although monosaccharides which can be utilized as the sweetener increase thereafter, free galactose rapidly increases simultaneously with the increase in monosaccharides. Therefore, by stopping the reaction at the time or near the time at which galactooligosaccharides reach the maximum yield, the monosaccharide mixture showing low content ratio of galactose can be obtained at a high yield.

The conditions for the reaction such as pH, temperature, and the like need to be determined to correspond to the characteristics thereof such that the two types of enzymes can act satisfactorily. In general, the galactosyl transfer reaction of β-galactosidase can be realized in the range between weak acid condition and neutral and glucose isomerase can act in range between neutral and weak basic condition. Therefore, the preferable pH is 5 to 8 and reaction temperature needs to be arranged to 30° to 9020 C., preferably 40° to 70° C. Since enzymes can be stabilized in a sugar solution of a high concentration, considerably high reaction temperature can be employed.

If β-galactosidase and glucose isomerase require metal ion, the required metal is added by a quantity with which the activity of the other enzyme is not inhibited. In general glucose isomerase requires magnesium salt to exhibit the activity thereof and β-galactosidase can be stabilized by magnesium salt or its activity cannot be inhibited by magnesium salt. Therefore, the addition of magnesium salt is the most suitably way in many cases.

The reaction time under the above-described reaction conditions is arranged as follows: first in a batch reaction, galactooligosaccharides which have increased along with reaction time begin to be reduced at a certain time after the hydrolysis reaction becomes predominant. Therefore, the reaction is stopped near the time when the maximum yield of galactooligosaccharide is reached. On the other hand, in the case of an immobilized enzyme reaction, the speed of supplying substrates is determined so as to making the quantity of galactooligosaccharides produced.

The product obtained from the reaction serves as a growth factor of bifidobacterium bacteria or serves as a sweetener by separating monosaccharides after the product has been subjected to a process of separating bacteria (in the case where are used), a process of decoloring and refining, a process of separating monosaccharides, a condensation process, and a drying process.

When the primary object to produce galactooligosaccharides, it is preferable that the reaction is conducted such that β-galactosidase and glucose isomerase, as described above, act simultaneously. Alternatively when production of a sweetener according to the second invention is desired, the reaction may be arranged such that only β-galactosidase is first effected and then glucose isomerase effected after the processing with this enzyme has been completed. A successive processing of the type described above exhibits an advantage that the two types of enzymes can be subjected to the processing under the most suitable conditions. Also according to the successive processing, a great portion of the galactose residue of the raw material lactose can be converted into galactooligosaccharides. Therefore, a sugar mixture in which the proportion of galactose is reduced can be obtained.

Both $\beta$-galactosidase and glucose isomerase can be inactivated by way of heating of the liquid to be reacted at 90° C. or higher for 5 to 10 minutes. As a result, the reaction by using with enzyme can be stopped. In cases where immobilized enzymes are used, the inactivation by way of heating is not realized before the separation.

Although the mixture obtained from the reaction after being subjected to the processings can be used as sweetener as it is, an excellent sweetener in terms of the degree and quality of sweetness can be obtained by removing galactooligosaccharides and non-reacted lactose having a low degree of sweetness and by conducting the refining in which only monosaccharides are taken. Monosaccharides and galactooligosaccharides whose molar weights are different from each other by a significant level can be readily separated from each other by known means for separating sugar such as column chromatography using activated charcoal or ion exchange resin.

The thus-obtained monosaccharide fraction contains the same quantity of glucose and fructose, the monosaccharides therefore containing galactose at an extremely low proportion of galactose. The composition of the monosaccharide fraction is substantially the same as that of high fructose corn syrup produced from starch, the monosaccharides displaying a high degree of sweetness of 1.0 to 1.2 and exhibiting an excellent quality of sweetness. Therefore, the monosaccharide fraction can be used as a sweet syrup as it is or after being condensed optionally, as the sweet syrup being similar to the above-described liquid sugar.

Galactooligosaccharides separated in the refining process can be, as is known, used as an excellent growth factor of bifidobacterium. Furthermore, the disaccharide fraction containing a large quantity of non-reacted lactose can be used again as a material for the reaction. Therefore, the yield of the raw material lactose units to be newly injected can be improved.

The method of preparation of the type described above has many advantages as follows:

(1) A sweetener composed from a monosaccharide mixture with fructose and glucose as the main ingredients and having an extremely reduced galactose content ratio can be obtained differing from the conventional simple lactose hydrolysis method from which a mixture containing glucose and galactose in the same quantity is prepared. The thus obtained sweetener has a significant degree of sweetness of 1.0 to 1.2 which is substantially the same level as that of saccharose with respect to the degree of sweetness of about 0.6 realized by the mixture containing glucose and galactose by the same quantity which is obtained from the conventional method and with respect to the degree of sweetness of 0.7 to 0.8 realized by the processing of the conventional mixture with glucose isomerase. Therefore, it can be used similarly to sucrose and its quantity can be halved to obtain the same sweetness, with little fear of excessive caloric intake. Furthermore, excellent sweetness quality which approximates the sweetness of sucrose can be obtained. Since the rate of the content of galactose can be reduced and the needed quantity can also be reduced, any evils of excessive galactose intake can be overcome in most cases. Therefore, the thus obtained sweetener can be widely used as sweetener which can be used alternatively to sucrose.

According to the method of preparing galactooligosaccharides, and in particular, according to the method in which $\beta$-galactosidase and glucoseisomerase are simultaneously used, glucose is not accumulated in the liquid to be reacted since glucose which is secondarily prepared when galactooligosaccharides are prepared by allowing $\beta$-galactosidase to act on lactose is successively converted into fructose. Therefore, any competing reaction can be eliminated in the transfer reaction, causing the yield of galactooligosaccharides to be improved. Furthermore, the yield of galactooligosaccharides can be improved by preventing the action of interrupting the activity of $\beta$-galactosidase. Since the quantity of transfer disaccharides and non-reacted lactose which are difficult to separate from galactooligosaccharides can be reduced, the refining process after the reaction can be readily conducted. Furthermore, the sugar mixture to be separated by the refining process becomes advantageous sweetener since the sugar mixture comprises fructose and glucose showing a considerably high degree of sweetness.

With the method of preparing a sweetener according to the present invention, the required quantity of enzymes can be reduced with respect to that required in the conventional hydrolysis method. Furthermore, the reaction can be conducted with the concentration of lactose maintained at a high level. Therefore, the reacting equipment and the condensing equipment can be reduced in size, causing, of course, reductions in thermal energy consumption and manufacturing costs.

Sweet syrup is, in general, stocked in the condensed manner in order to prevent putrefaction due to growth of microorganisms. However, conventional syrup obtained by hydrolyzing lactose encounters a problem in terms of handling and stocking since it cannot be satisfactorily condensed, because it contains a large quantity of galactose having low solubility, that easily crystallizes. However, since the syrup according to the present invention contains a low proportion of galactose, the fear of crystal deposition can be eliminated, it can be satisfactorily condensed and stocked.

Recently, an excellent sweetener which can replace sugar has been strongly desired from the viewpoint of prevention of tooth decay. The present invention can meet such a desire. In addition, many dairy nations because of their industrial structure depend on imports sucrose for large portion of the starch necessary for manufacturing sweeteners. The manufacturing of an excellent sweetener with the method according to the present invention in which whey is utilized has many advantages, for such countries in which whey which is an un-used resource creating environmental pollution.

DESCRIPTION OF THE PREFERRED EMBODIMENTS

Examples of the present invention will be described below.

EXAMPLE 1

350 g of lactose was added to 0.05M potassium phosphate buffer solution (pH 6.0) and heated to solution for a total quantity of 500 ml. Then, 1500 units of $\beta$-galactosidase lactase Y-400 (manufactured by Yakult Honsha i Co., Ltd.) derived from Aspergillus oryzae and 50 g of immobilized glucose isomerase GODO-AGI (310 IGIU/g manufactured by Godo Shusei Co., Ltd.) were added to the solution before addition of magnesium sulfate so as to become 5mM. The thus-prepared liquid was reacted at 60° C. over night while being shaken. Immobilized glucose isomerase was filtered, and then the liquid to be reacted was heated so as to inactivate $\beta$-galactosidase. Then, 5g of activated carbon was added to the liquid in which the enzyme reaction had been stopped and the liquid was subjected to a decoloring processing. As a result, a colorless transparent sugar liquid was obtained.

EXAMPLE 2

30g lactose was added to 0.05M potassium phosphate buffer solution (pH 6.0) and heated to solution for a total quantity of 45 ml. Then, 27 units of $\beta$-galactosidase lactase derived from Bullera Singularis, 5 g of immobilized glucose isomerase GODO-AGI, and IM magnesium sulfate were added before addition of water so as to make the total quantity 50 ml. The thus-prepared liquid was reacted at 55° C. over night while being shaken. Immobilized glucose isomerase was filtered, and then the liquid to be reacted was heated so as to inactivate $\beta$-galactosidase. Then, 1g activated carbon was added to the liquid in which the enzyme reaction had been stopped and the liquid was subjected to a decoloring processing. As a result, a colorless transparent sugar liquid was obtained.

EXAMPLE 3

25g of lactose was added to 0.05M potassium phosphate buffer solution (pH 7.0) and heated to solution for a total quantity of 45 ml. Then, 200 units of $\beta$-galactosidase Biolacta (manufactured by Daiwa Chemicals Co., Ltd.) derived from Bacillus circulance, 5 g of immobilized glucose isomerase GODO-AGI, and 0.25 ml IM-magnesium sulfate were added before addition of water so as to make the total quantity 50 ml. The thus-prepared liquid was reacted at 55° C. over night while being shaken. Immobilized glucose isomerase was filtered, and then the liquid to be reacted was heated so as to inactivate $\beta$-galactosidase. Then, 1g activated carbon was added to the liquid in which the enzyme reaction had been stopped and the liquid was subjected to a decoloring processing. As a result, a colorless transparent sugar liquid was obtained.

EXAMPLE 4

25g of lactose was added to 0.05M potassium phosphate buffer solution (pH 7.0) and heated to solution for a total quantity of 45 ml. Then, 300 units of $\beta$-galactosidase of Lactobacillus bulgaricus ATCC11842 which had been prepared in a usual manner, 5 g of immobilized glucose isomerase GODO-AGI, and 0.25 ml IM-magnesium sulfate were added before addition of water so as to make the total quantity 50 ml. The thus-prepared liquid was reacted at 50° C. over night while being shaken. Immobilized glucose isomerase was filtered, and then the liquid to be reacted was heated so as to inactivate $\beta$-galactosidase. Then, 1g activated carbon was added to the liquid in which the enzyme reaction had been stopped and the liquid was subjected to a decoloring processing. As a result, a colorless transparent sugar liquid was obtained.

EXAMPLE 5

25g of lactose was added to 0.05M potassium phosphate buffer solution (pH 7.0) and heated to solution for a total quantity of 45 ml. Then, bacteria suspension (300 units as $\beta$-galactosidase) of streptococcus thermophilus YIT2046 obtained from a culture, 5 g of immobilized glucose isomerase GODO-AGI, and 0.25 ml IM-magnesium sulfate were added before addition of water so as to make the total quantity 50 ml. The thus-prepared liquid was reacted at 50° C. over night while being shaken. 1g of activated carbon was added to liquid to be reacted from which immobilized glucose isomerase and bacteria of streptococcus thermophilus had been filtered, and then the liquid was subjected to a decoloring processing. As a result, a colorless sugar liquid was obtained.

The compositions of the products are shown in the following table, and the results of comparative examples carried out similarly to the examples but without the addition of immobilized glucose isomerase are also shown.

| | Composition of Products (unit: weight percent) | | | | | |
|---|---|---|---|---|---|---|
| | | | Monosaccharide* | | | |
| | galactooligosaccharide | Disaccharide | Glc | Fru | Gal | Total |
| Example 1 | 30 | 35 | 14 | 14 | 7 | 35 |
| Comparative Example 1 | 29 | 43 | 21 | 0 | 7 | 28 |
| Example 2 | 48 | 33 | 9 | 9 | 1 | 19 |
| Comparative Example 2 | 42 | 40 | 17 | 0 | 1 | 18 |
| Example 3 | 44 | 32 | 12 | 11 | 1 | 24 |
| Comparative Example 3 | 38 | 42 | 19 | 0 | 1 | 20 |
| Example 4 | 33 | 25 | 16 | 16 | 10 | 42 |
| Comparative Example 4 | 32 | 40 | 21 | 0 | 7 | 28 |
| Example 5 | 32 | 29 | 17 | 17 | 5 | 39 |
| Comparative Example 5 | 30 | 33 | 30 | 0 | 7 | 37 |

*where Glc: glucose, Fru: fructose, Gal: galactose

Next, an example of a method of preparing a sweetener according to the present invention will be described.

EXAMPLE 6

4kg of an edible grade lactose was dissolved in 2.4 liters of hot water. Then, a buffer solution of pH 4.5 and 40,000 units of $\beta$-galactosidase (Lactase Y-400 manufactured by Yakult Honsha Co., Ltd.) derived from Aspergillus oryzae were added to the solution so as to be reacted at 70° C. for 2 hours. The, liquid to be reacted was heated at 90° C. for 10 minutes so as to inactivate β-galactosidase before being cooled down to 60° C. The pH was adjusted to 7.5 and magnesium sulfate was added so as to make the concentration thereof 5mM. Then, 30,000 units of immobilized glucose isomerase (GODO-AGI) was added so as to react for 16 hours. After the reaction, immobilized glucose isomerase was filtered, and a filtration was conducted with powder activated carbon and cerite added before conducting desalting by using an ion exchange resin. The obtained sugar liquid comprised the solid content having a concentration of 60%, the sugar in the solid content being composed of 28.4% galactooligosaccharides, 52.4% disaccharides, 8.0% of glucose, 8.1% of fructose, and 3.1% of galactose. The thus obtained sugar liquid was successively processed by using columns (two stainless steel columns each having an inner diameter of 35.5 mm and length of 910 mm and connected in series) with Unibeads UBK-530 (Na type), a strong acid cation ion exchange resin for chromatography. As a result, the liquid was divided into a galactooligosaccharide fraction, a lactose faction, and a monosaccharide fraction. The yield (weight percent with respect to original lactose) and composition of each of the fractions were as follows:

|  | Monosaccharide | Lactose | Oligosaccharide |
| --- | --- | --- | --- |
| Yield (%) | 16 | 55 | 22 |
| Glucose (%) | 36.9 | 2.7 | 0.1 |
| Fructose (%) | 43.7 | 1.9 | 0.0 |
| Galactose (%) | 16.4 | 0.8 | 0.0 |
| Lactose (%) | 3.0 | 79.6 | 14.8 |
| Oligosaccharide (%) | 0.0 | 15.0 | 85.1 |

The above-described monosaccharide fractions were condensed to a concentration of the solid content of 75% so that sweet syrup was obtained, the syrup displaying a mild refreshing quality of sweetness with a degree of sweetness of 1.1.

The recovered lactose fraction (the solid content was 2.3 kg) was condensed so as to be utilized as the material for the next reaction. That is, 1.7 kg of lactose was newly added to condensed liquid before being subjected to the enzyme treatment and chromatographic separation which were conducted to be similar to the above described methods. The yield of monosaccharide fraction with respect to lactose was 45%.

EXAMPLE 7

4kg of a food grade lactose was dissolved in a 0.05M potassium phosphate buffer solution (pH 6.0) so as to make the overall quantity 6.0 l. Then, 3600 units of partial refined enzymes (having β-galactosyl transfer activity) derived from *Bullera Singularis* were added as β-galactosidase, and 80,000 units of glucose isomerase (GODOAGI) and IM magnesium sulfate of 33 ml were added, respectively before addition of water so as to make the overall quantity 6.7 l. The liquid was reacted at 55° C. over night while being shaken Then, glucose isomerase was removed from the liquid by filtration before being heated so as to inactivate β-galactosidase.

Powder activated carbon and cerite were added to the obtained enzyme reaction mixture liquid before being subjected to filtration. Then, it was desalted by using an ion exchange resin. The obtained sugar liquid comprised a solid content having a concentration of 60%, the sugar in the solid content being composed of 48.1% galactooligosaccharides, 32.9% disaccharides, 9.1% glucose, 9.0% fructose, and 0.9% galactose. The thus obtained sugar liquid was separated by using columns similar to those used in Example 6. As a result, the following results were obtained:

|  | Monosaccharide | Lactose | Oligosaccharide |
| --- | --- | --- | --- |
| Yield (%) | 19 | 30 | 45 |
| Glucose (%) | 42.7 | 1.8 | 0.0 |
| Fructose (%) | 49.6 | 1.0 | 0.0 |
| Galactose (%) | 5.0 | 0.2 | 0.0 |
| Lactose (%) | 2.7 | 74.3 | 9.9 |
| Oligosaccharide (%) | 0.0 | 22.7 | 90.1 |

The above-described monosaccharide fractions were condensed and subjected to the desalting and decoloration processings by using an ion exchange resin, so that a sweet syrup having a concentration of the solid component of 75% was obtained, the syrup displaying colorless transparent characteristics and a mild refreshing quality of sweetness with a degree of sweetness of 1.2.

What is claimed is:

1. A method of preparing a mixture of galactooligosaccharides having the following formula:

Gal-(Gal)n-Gcl where Gal represents a galactose residue, Glc represents a glucose residue, and n represents an integer between 1 and 4 and monosaccharides by treating a lactose solution with microorganisms containing β-galactosidase or isolated β-galactosidase wherein said β-galactosidase has galactosyl transfer activity sufficient to limit the production of free galactose to less than about 16.4% of the monosaccharides produced; and converting a portion of glucose prepared by the β-galactosidase treatment into fructose by
  having glucose isomerase coexist in the lactose solution to be treated or by adding glucose isomerase after completion of the treatment.

2. A method according to claim 1, wherein glucose isomerase is sued together when said microorganisms containing β-galactosidase or said β-galactosidase act upon said lactose.

3. A method according to claim 1, wherein glucose isomerase is made to act after said microorganisms containing β-galactosidase or said β-galactosidase have acted on said lactose.

4. A method of preparing a sweetener comprising: preparing a mixture of galactooligosaccharides having the following formula:

Gal-(Gal)n-Glc where Gal represents a galactose residue, Glc represents a glucose residue, and an represents an integer between 1 and 4 and monosaccharides by treating a lactose solution with microorganisms containing β-galactosidase or isolated β-galactosidase wherein said β-galactosidase has galactosyl transfer activity sufficient to limit the production of free galactose to less than about 16.4% of the monosaccharides produces; and converting a portion of glucose prepared by the β-galactosidase treatment into fructose by
  having glucose isomerase coexist in the lactose solution to be treated or by adding glucose isomerase after completion of the treatment; and then separating monosaccharides whose main principle ingredients are glucose and fructose from the mixture.

5. A method according to claim 4, wherein glucose isomerase is used together when said microorganisms containing β-galactosidase or said β-galactosidase act on said lactose.

6. A method according to claim 4, wherein glucose isomerase is made to act after said microorganisms containing β-galactosidase or said β-galactosidase have acted on said lactose.

7. A method according to any of claims 1 to 6, wherein the concentration of said lactose ranges between 20 and 80%.

8. A method according to any of claims 1 to 6, wherein magnesium salt is present in said lactose solution.

9. A method according to any of claims 4 to 6, wherein said monosaccharides are separated by way of column chromatography.

10. The method of claim 1 wherein the amount of free galactose produced is less than about 10% of the monosaccharides produced.

11. The method of claim 4, wherein the amount of free galactose produced is less than about 10% of the monosaccharides produced.

* * * * *

UNITED STATES PATENT AND TRADEMARK OFFICE
CERTIFICATE OF CORRECTION

PATENT NO. : 5,032,509

DATED : July 16, 1991

INVENTOR(S) : Keisuke Matsumoto, et al

It is certified that error appears in the above-identified patent and that said Letters Patent is hereby corrected as shown below:

On the title page and column 1, lines 1 - 2, should read

--METHOD OF PREPARING GALACTOOLIGOSACCHARIDES--.

Signed and Sealed this

First Day of December, 1992

Attest:

DOUGLAS B. COMER

Attesting Officer

Acting Commissioner of Patents and Trademarks